United States Patent [19]

McConaghy

[11] Patent Number: 4,515,017
[45] Date of Patent: May 7, 1985

[54] OSCILLATING ULTRASOUND SCANHEAD

[75] Inventor: Robert F. McConaghy, Kirkland, Wash.

[73] Assignee: Advanced Technology Laboratories, Inc., Bellevue, Wash.

[21] Appl. No.: 553,716

[22] Filed: Nov. 21, 1983

[51] Int. Cl.³ .............................................. G01N 29/04
[52] U.S. Cl. ....................................... 73/618; 73/633; 128/660
[58] Field of Search ................ 73/633, 634, 618, 619; 128/660

[56] References Cited

U.S. PATENT DOCUMENTS

| 3,927,661 | 12/1975 | Takemura . | |
| 3,955,561 | 5/1976 | Eggleton . | |
| 4,130,021 | 12/1978 | Mueller et al. | 73/633 |
| 4,130,022 | 12/1978 | Goodrich et al. | 73/633 |
| 4,185,501 | 1/1980 | Proudian et al. | 128/660 |
| 4,215,585 | 8/1980 | Kunii et al. | 73/633 |
| 4,377,088 | 3/1983 | Evert | 73/633 |
| 4,399,703 | 8/1983 | Matzuk | 73/633 |
| 4,426,886 | 1/1984 | Finsterwald | 73/633 |
| 4,462,255 | 7/1984 | Guess | 73/633 |

*Primary Examiner*—Howard A. Birmiel
*Attorney, Agent, or Firm*—Lawrence S. Levinson; Sanford J. Asman

[57] ABSTRACT

The scanhead uses a shaft mounted, oscillating rotor driven by a shaft mounted rotor. Energy storage and repulsive means, provided by magnetic "bumpers" helps to reverse the direction of motion of the rotor at the end of the scan angle.

8 Claims, 8 Drawing Figures

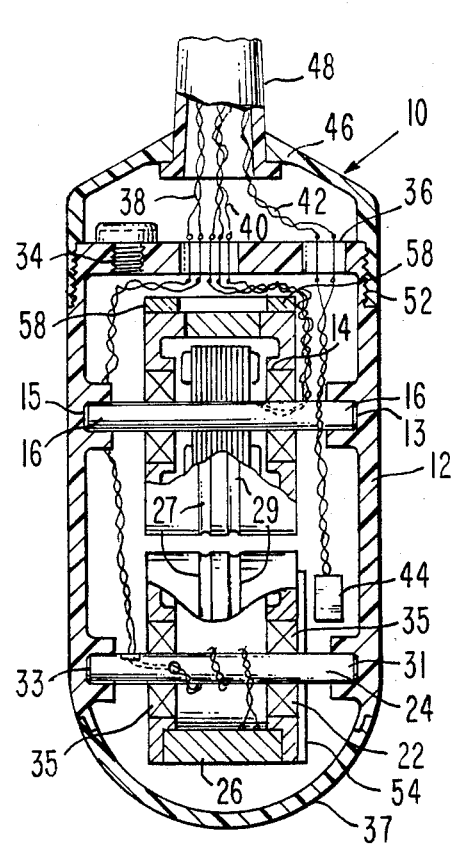
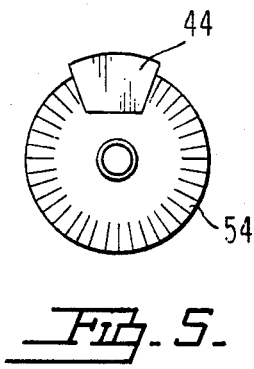
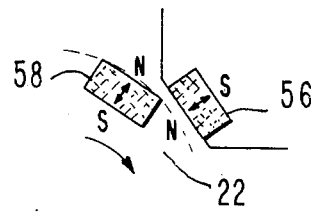
Fig. 2.
Fig. 5.
Fig. 6.

OSCILLATING ULTRASOUND SCANHEAD

BACKGROUND OF THE INVENTION

The present invention relates to an oscillating scanhead drive for use with medical diagnostic ultrasound equipment. In particular, the invention relates to a drive for a scanhead of the type used in an ultrasound sector scanner.

There are numerous types of ultrasound sector scanners presently used for medical diagnosis. These scanners employ two basic types of apparatus to impart mechanical movement. In the first type of apparatus, from two to four transducers are mounted on a rotating armature, and an individual one of these transducers is activated for transmission and reception of ultrasound energy at any given time. This type of scanhead, typically called a "rotary" scanhead, while in common use, is very expensive to produce for a number reasons. In particular, each of the transducers used in the scanhead must be matched to the other transducers in order to avoid flickering or degradation of image quality when the unit switches from one transducer to the next one. Accordingly, hand matching of transducers, a labor intensive, expensive procedure, is employed to select matched transducers to be mounted in a rotor. Then, once matched transducers are obtained, it is critical to mount them all on the same axis on the rotating armature in order to avoid problems of image flicker on the screen as the different transducers are activated.

In another type of ultrasound scanhead called an "oscillating" scanhead or a "wobbler", a single transducer is used. That transducer is mounted in a mechanism which oscillates back and forth. The oscillating scanhead has the advantage of being less expensive to produce in that only a single transducer is required, thereby avoiding the problems associated with matching transducers and aligning them on the same axis. A problem, however, with oscillating scanheads is that they typically vibrate quite a bit due to their oscillatory operation. Accordingly, it would be highly desirable to have an oscillating mechanism which is always dynamically balanced.

SUMMARY OF THE INVENTION

The present invention relates to an oscillating mechanism which is always in dynamic balance. The invention includes a system which provides energy storage to help yield the maximum possible frame rate while imposing the least amount of stress on the mechanism. The present invention also provides an efficient means for absorbing and returning energy to the system. In accordance with the present invention, a pair of parallel shafts each holding a massive element are juxtaposed adjacent to one another whereby their moments of inertia are equal. The shafts are interconnected so that a clockwise rotation of the first shaft induces a corresponding counterclockwise rotation of the second shaft. The dynamic balance of the two shafts is accomplished by having the mass on each shaft in complete dynamic balance and by having the inertias of each mass related to the instantaneous angular velocity of each shaft (as determined by the ratio of movement between the shafts). The relationship requires that the moment of inertia of the first shaft times the angular velocity of the first shaft equal the moment of inertia of the second shaft times the angular velocity of the second shaft. In accordance with the invention, a novel magnetic bumper means is used to store rotational energy and restore it to the system, in much the same manner as a mechanical spring.

BRIEF DESCRIPTION OF THE DRAWING

FIG. 2 is a side cross-sectional view of the oscillating ultrasound scanhead of FIG. 1;

FIG. 5 is an illustration of the encoder disk used in the present invention;

FIG. 6 is a top view illustrating the manner in which the magnetic repulsion system operates;

DETAILED DESCRIPTION OF THE PREFERRED EMBODIMENT

Figure 1:
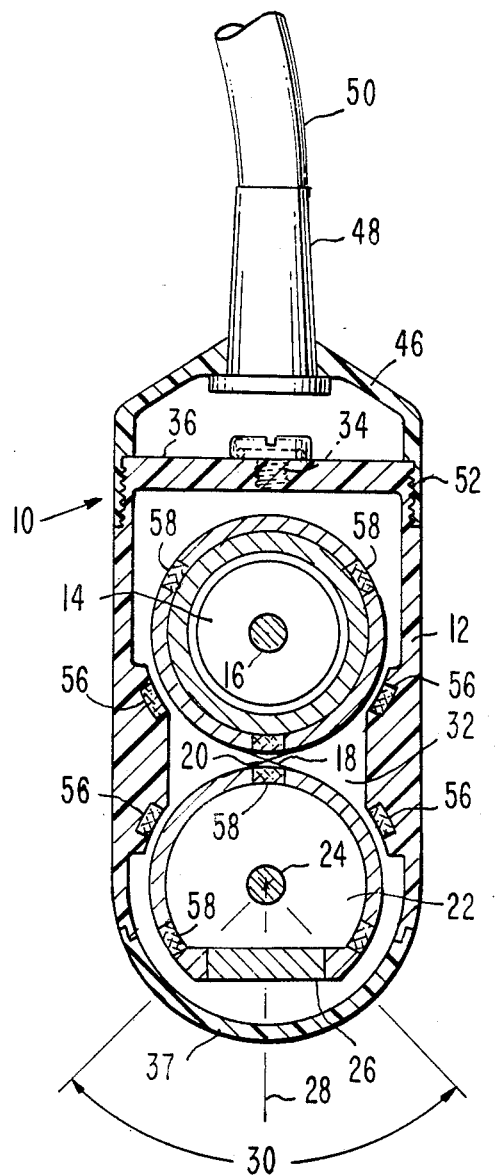
FIG. 1 is a top cross-sectional view of an ultrasound scanhead of the type employing the present invention.

Referring now generally to FIGS. 1 and 2, the oscillating scanhead 10 of the present invention is shown. The scanhead 10 is comprised of a housing 12 which contains a motor 14 mounted on a shaft 16. In the preferred embodiment of the invention, the motor 14 is a three phase brushless DC motor. As shown in FIG. 2, the ends 13, 15 of the shaft 16 are mounted in the housing 12. Accordingly, when the motor 14 rotates, the body of the motor 14 rotates around a stationary shaft 16, as opposed to a more conventional mounting arrangement in which the motor housing is fixed and the shaft rotates.

Figure 3:
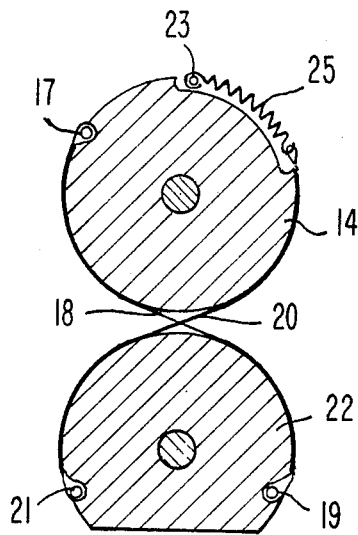
FIG. 3 is an illustration of the manner in which the two shafts are connected in the present invention.
Figure 4:
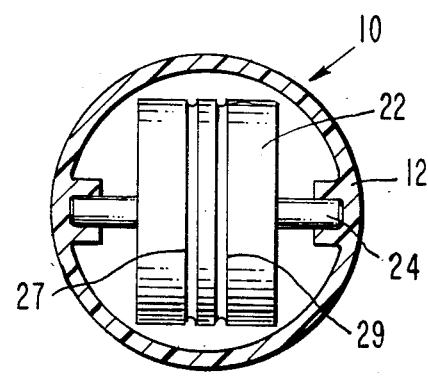
FIG. 4 is an end cross-sectional view showing the inner portion of the rotor of the ultrasound scanhead as viewed from the motor.

With reference to FIG. 3, in the preferred embodiment of the invention, the motor 14 has a cable 18 attached to its body at a first attachment point 17. The other end of the cable 18 is attached to a second attachment point 19 on a rotor 22. A second cable 20 is attached to a third attachment point 21 on the rotor 22 and to a fourth attachment point 23 on the motor 14. The second cable 20 is attached to the fourth attachment point 23 through a tensioning spring 25, as shown. The cables 18, 20 are fitted into a pair of grooves 27, 29 in the body of the motor 14 and the rotor 22 which are shown in FIGS. 2 and 4 (with the cables 18, 20 removed for clarity). The rotor 22 is mounted on a hollow, stationary shaft 24 whose ends 31, 33 are attached to the housing 12, as shown in FIG. 2. Bearings 35 permit the rotor 22 to rotate on the shaft 24. The shafts 16, 24 are substantially parallel to one another. The rotor 22 holds an ultrasonic transducer 26 which is typically a piezoelectric transducer.

As shown in FIG. 1, when the rotor 22 oscillates, the axis 28 of the transducer 26, which is typically aligned with a radial eminating from the center of the shaft 24 of the rotor 22, oscillates through a scan angle 30. The housing 12 encloses a cavity 32 in which the motor 14 and the rotor 22 are located. The housing 32 is completely filled with an acoustic coupling fluid, such as mineral oil. The acoustic coupling fluid is injected into the cavity 32 through a fill port 34 which extends through a bulkhead 36. At the front of the scanhead 10, there is an end cap 37 which is made of a material, such as plastic, which is substantially transparent to ultrasound waves transmitted and received by the transducer 26. Signal wires 38 (shown in FIG. 2, but omitted from FIG. 1 for clarity) which go to the transducer 26, and the three phase power wires 40, which go to the motor 14, pass through the bulkhead 36, as shown in FIG. 2. The signal wires 38 pass into the center of the hollow rotor 22 via the hollow shaft 24, as shown, and they are electrically connected to the transducer 26 in the standard manner. Also, wires 42 which go to a position sensing head 44 containing LED light sources and phototransistor pickups (not shown), pass through the bulkhead 36. A rear cap 46, which holds a strain relief 48 that connects to a cable 50, is screwed onto the threaded exterior wall 52 of the bulkhead 36 in order to protect the fill port 34 and the various wires 38, 40, 42.

An encoder disk 54, shown also in FIG. 5, is attached to the rotor 22 as shown in FIG. 2. In the preferred embodiment of the invention, the encoder disk 54 is glued to the rotor 22. The encoder disk 54 is preferably comprised of a disk of glass with alternating reflective and non-reflective lines which are observed by the photoelectric read head 44 in a manner well known in the art. The combination of the photoelectric read head 44 and the encoder disk 54 provide a system for accurately determining the position of the rotor 22, and consequently the position of the axis 28 of the piezoelectric transducer 26.

Referring now generally to FIGS. 1 and 6, the scanhead 10 also includes a number of fixed magnets 56 which are mounted in the housing 12. As shown in FIG. 6, the fixed magnets 56 have an orientation such that one pole of each of the fixed magnets 56, i.e., the north pole as shown in FIG. 6, extends out of the housing 12 toward either the rotor 22 or the motor 14. Rotating magnets 58 are mounted on the rotor 22 and on the motor 14. The orientation of the rotating magnets 58 is such that the same pole, i.e., the north pole, extends out from the motor 14 or rotor 22. Accordingly, as the motor 14 rotates in a particular direction, i.e. clockwise, the fixed and rotating magnets 56, 58 will interact in repulsion as the rotating magnets 58 get close to the fixed magnets 56. Accordingly, the magnetic field provides an energy storage and repulsion system, similar to a mechanical spring, which provides for very smooth operation of the piezoelectric transducer rotor 22. In the preferred embodiment of the invention, the magnets 56, 58 are samarium-cobalt magnets. As is well known in the art, appropriate signals are sent to the three phase brushless DC motor 14 in order to "kick" the motor 14 to add any energy which is needed as a result of inevitable losses in the system.

In the preferred embodiment 10, there are a total of 20 magnets 58, 56 with three rotating magnets 58 mounted on each of the upper and lower portions of the motor 14 and the rotor 22, respectively, for a total of twelve rotating magnets 58. There are also eight fixed magnets 56 mounted on the housing 12, with four each on the top (See FIG. 1), and on the bottom (See FIG. 2).

In the operation of the preferred embodiment of the invention, a standard motor controller (not shown) may be used to control the operation of the three phase motor 14. Feedback information relating to the position of the rotor 22 is provided to the motor controller by the position sensing head 44 from information derived from the encoder disk 54. Accordingly, the motor controller always "knows" where the transducer 26 is pointing in the scan angle 30. The overall system is arranged to be dynamically balanced, and in combination with the energy storage provided by the magnets 54, 56, very little energy is required to keep the rotor 22 oscillating.

Figure 7:
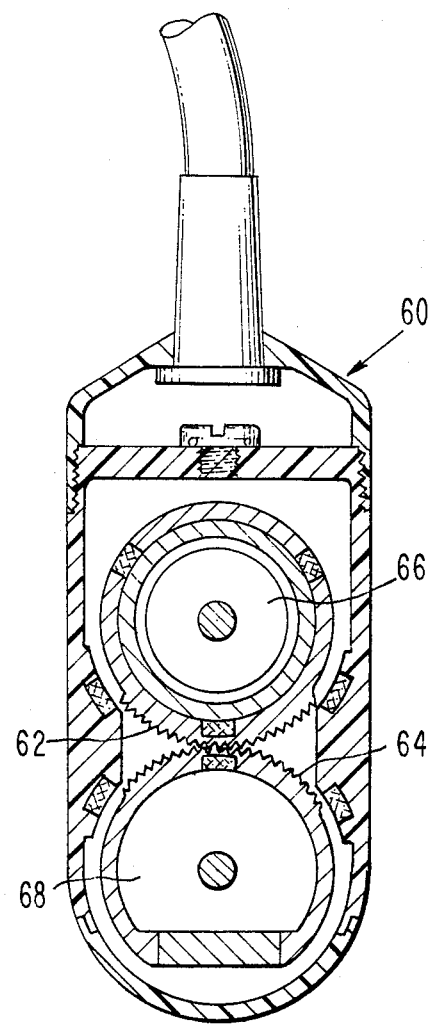
FIG. 7 is a top cross-sectional view of a second embodiment of the present invention.
Figure 8:
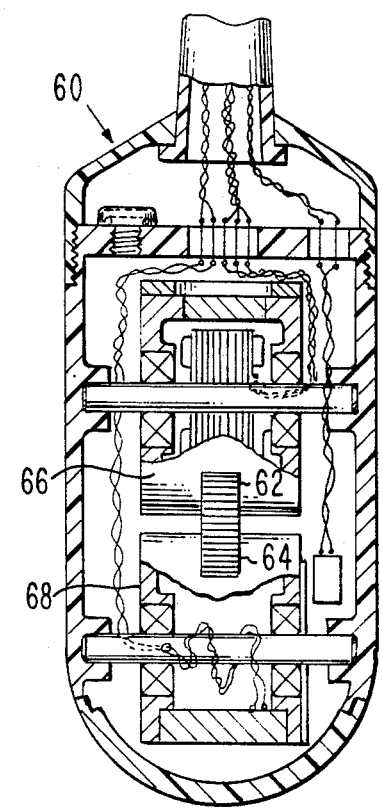
FIG. 8 is a side cross-sectional view of the embodiment of FIG. 7.

Referring now to FIGS. 7 and 8, an alternative embodiment 60 of the present invention is shown. In the alternative embodiment 60, instead of a cable drive system, as used in the preferred embodiment, a gear drive system is used. There are gear segments 62, 64 on the motor 66 and on the rotor 68, respectively. Otherwise, the embodiment 60 operates in a manner identical to the preferred embodiment 10 which uses the cables 18, 20 to drive it. It has been found that the cable drive system is quieter and more compact, and it provides smoother operation than the gear drive system. Therefore, the cable system is preferred. However, the gear drive system is considered, also, to be within the scope of the present invention.

I claim:
1. An oscillating ultrasound scanhead comprising:
   (a) a housing;
   (b) a reversible electric motor mounted in said housing, the shaft of said motor being fixedly mounted to said housing:
   (c) an ultrasound transducer mounted on a rotor, said rotor being rotatably mounted on a rotor shaft which is substantially parallel to said motor shaft, whereby said rotor can rotate at least through an angle corresponding to the scan angle of said oscillating ultrasound scanhead;
   (d) means for driving said rotor by said motor; and
   (e) repulsion and energy storage means comprised of fixed magnets mounted in said housing and rotating magnets mounted on said motor and rotor, whereby said magnets are arranged to repel one another at the ends of said scan angle due to the magnetic fields generated therebetween.

2. The oscillation ultrasound scanhead of claim 1 further comprising encoder means for determining the position of said rotor.

3. The oscillating ultrasound scanhead of claim 2 wherein said encoder means is comprised of a reflective disk mounted on said rotor and a photoelectric position sensing head mounted in said housing adjacent to said rotor.

4. The oscillating ultrasound scanhead of claim 1 wherein said rotor shaft is hollow and signal wires connected to said transducer pass through said shaft.

5. The oscillating ultrasound scanhead of claim 1 further comprising a bulkhead which closes off said housing to define a cavity therein, said cavity containing said motor and said rotor.

6. The oscillating ultrasound scanhead of claim 5 wherein said cavity is filled with an ultrasound conducting fluid.

7. The oscillating ultrasound scanhead of claim 5 wherein said means for driving said rotor comprises a pair of cables connected between said motor and said rotor.

8. The oscillating ultrasound scanhead of claim 5 wherein said means for driving said rotor comprises a interactive gear segments on said motor and said rotor.

* * * * *

UNITED STATES PATENT AND TRADEMARK OFFICE
CERTIFICATE OF CORRECTION

PATENT NO. : 4,515,017
DATED : May 7, 1985
INVENTOR(S) : Robert F. McConaghy

It is certified that error appears in the above–identified patent and that said Letters Patent are hereby corrected as shown below:

Claim 2, Line 1, "oscillation" should read --oscillating--.

Signed and Sealed this

Thirteenth Day of August 1985

[SEAL]

Attest:

DONALD J. QUIGG

Attesting Officer

Acting Commissioner of Patents and Trademarks